United States Patent [19]
Wood et al.

[11] Patent Number: 4,748,145
[45] Date of Patent: * May 31, 1988

[54] CATALYSTS HAVING ALKOXIDE-MODIFIED SUPPORTS AND METHOD OF INCREASING THE CATALYTIC ACTIVITY OF A CATALYTIC METAL

[75] Inventors: Clayton D. Wood, Framingham, Mass.; Philip E. Garrou, Charlotte, N.C.; Edward F. Gleason, III, Danvers, Mass.; Iwao Kohatsu, Lexington, Mass.

[73] Assignee: The Dow Chemical Company, Midland, Mich.

[*] Notice: The portion of the term of this patent subsequent to Feb. 10, 2004 has been disclaimed.

[21] Appl. No.: 12,924

[22] Filed: Feb. 9, 1987

Related U.S. Application Data

[60] Division of Ser. No. 809,544, Dec. 16, 1985, which is a continuation-in-part of Ser. No. 655,991, Sep. 28, 1984, Pat. No. 4,559,364, which is a division of Ser. No. 567,112, Dec. 30, 1983, abandoned.

[51] Int. Cl.$^4$ .................. B01J 21/04; B01J 21/06; B01J 21/08; B01J 23/64

[52] U.S. Cl. .................. 502/332; 502/242; 502/246; 502/258; 502/259; 502/260; 502/261; 502/262; 502/325; 502/333; 502/334; 502/335; 502/336

[58] Field of Search ............. 502/242, 246, 258, 259, 502/260, 261, 262, 325, 332, 333, 334, 335, 336

[56] References Cited

U.S. PATENT DOCUMENTS

| | | | |
|---|---|---|---|
| 3,873,469 | 3/1975 | Foster et al. | 502/242 |
| 4,076,792 | 2/1978 | Foster et al. | 502/334 |
| 4,171,320 | 10/1979 | Vannice et al. | 518/715 |
| 4,269,737 | 5/1981 | Grenoble et al. | 502/204 |
| 4,376,721 | 3/1983 | Huang | 502/171 |
| 4,400,306 | 8/1982 | Dria et al. | 502/171 |

OTHER PUBLICATIONS

"C$_{18}$ Fats Hydrogenation with Pd Catalysts", La Chimica E L'Industria, vol. 65, No. 11, 688–693, (1983).

*Primary Examiner*—W. J. Shine
*Attorney, Agent, or Firm*—M. F. Zuckerman

[57] ABSTRACT

A catalyst composition comprising a catalytic metal and a support, the support being prepared by depositing a metal alkoxide on a core support, then calcining the support.

16 Claims, 2 Drawing Sheets

CATALYSTS HAVING ALKOXIDE-MODIFIED SUPPORTS AND METHOD OF INCREASING THE CATALYTIC ACTIVITY OF A CATALYTIC METAL

CROSS-REFERENCE TO RELATED APPLICATION

This is a divisional of application Ser. No. 809,544, filed Dec. 16, 1985 which is a continuation-in-part of application Ser. No. 655,991, filed Sept. 28, 1984 and now U.S. Pat. No. 4,559,364, which is a divisional of application Ser. No. 567,112, filed Dec. 30, 1983, now abandoned.

BACKGROUND OF THE INVENTION

The present invention relates to supported metal catalysts.

It is known to employ metal alkoxides in the preparation of solid catalysts. The reasons for employing the metal alkoxides vary considerably, as can be seen from the following description of the use of catalysts in the literature. For example, U.S. Pat. No. 3,873,469 discloses the preparation of metal catalysts for the purification of automobile exhaust gases. The catalysts are prepared by impregnating a precious metal such as platinum, palladium, rhodium, iridium, ruthenium or mixtures thereof onto a monolithic honeycomb structure. The honeycomb structure is composed of refractory compounds of low surface area. The chemically inert and refractory nature of this honeycomb is extremely important, as it should not undergo any drastic transformations during the extreme conditions encountered in typical automobile exhaust systems. However, impregnation of precious metals onto such a support surface to obtain a thermally stable catalyst having reasonably high metal dispersion is practically impossible. This difficulty is overcome in the teaching of said patent by employing a metal alkoxide to "wash coat" the low surface area honeycomb to obtain a honeycomb having higher surface area. The higher surface area support is suitable for catalyst preparation.

Similiarly, U.S. Pat. No. 4,076,792 discloses the use of metal alkoxides to prepare layered support coatings on monolithic honeycombs to make catalysts having both platinum and rhodium deposited on a wash coated honeycomb. The wash coating method comprises the impregnation of the selected support structure with the lower alkoxides of metals followed by the in situ hydrolysis of the metal alkoxides to form an adherent coating of hydrous metal oxides. The coated support structure may then be fired to convert the hydrous metal oxides to an oxide support coating of very high surface area and good porosity.

The use of metal alkoxides to supply alkali metal ions in a nonaqueous form is described by R. Hombek, J. Kijenski, and S. Malinowski (Warsaw, Poland) in a paper presented at the Second International Symposium on Scientific Bases for the Preparation of Heterogeneous Catalysts, held at Louvain-la-Neuve, Belgium, on September 4-7, 1978 (Proceedings published as *Studies in Surface Science and Catalysis*, Vol. 3, by Elsevier Scientific Publishing Company, Amsterdam/Oxford/New York, 1979; pages 595-603). Many industrial catalysts, especially for dehydrogenation and cracking processes, are modified by the controlled dosing of alkali metal ions to suppress the unwanted strong acidity of the catalyst carrier or support. The new alkali impregnation procedure, using alkali metal alkoxides in alcoholic solutions, avoids the reaction of water with dehydrated alumina support surfaces; this is particularly important because the water causes considerable changes in the properties of catalysts prepared by the aqueous alkali-hydroxide addition method.

Still another development reported by M. Glinski and J. Kijenski (same Polish group as above) is the method of impregnation with vanadyl tri-isobutoxide to prepare vanadium-alumina and vanadium-silica catalyst systems. This is described by the Polish authors in their paper presented at the Third International Symposium on Scientific Bases for the Preparation of Heterogeneous Catalysis, Vol. 16, 1983; pages 553-561. As in the case of impregnation with alkali-metal alkoxides, the application of vanadyl alkoxide in a non-aqueous medium avoids the secondary effects caused by the interaction of water with the dehydrated alumina or silica surface. Following the alkoxide impregnation, the resultant product was calcined in a stream of dry air at 573° K. for 3 hours to obtain the respective vanadium-alumina or vanadium-silica catalysts. The catalysts can further be reduced if necessary.

The principle of bringing the catalytically active material or materials in the form of an alkoxide precursor, followed by hydrolysis or thermal decomposition to obtain the final supported metal oxide or metal catalyst, is also the basis of the invention of U.S. Pat. No. 4,400,306. This method of catalyst preparation comprises: impregnating a preformed catalyst support with a solution of an alkoxide of at least one metal selected from V, Mo, Sb, Cu, Nb, Ta, Zn, Zr, B and mixtures thereof; contacting the impregnated support with a solution of at least one additional catalyst component to form the catalyst in situ, and drying or calcining the thus formed catalyst. The preformed catalyst support in such cases can be of different types and shapes, e.g., non-porous or microporous fluidizable powders, pellets or tablets, extrudates, monoliths and similar forms. The patent teaches (U.S. Pat. No. 4,400,306; column 3, lines 22-31) that "the use of metal alkoxides in the impregnation step is advantageous because the alkoxide reagent represents an extremely pure source of the metal and metal oxide reagents, unlike water-soluble salts such as the alkali metal or sulfur-containing salts which carry possibly unwanted counter-ions into the support material for incorporation into the catalyst. Upon heating or calcining, the alcohol adduct of the alkoxide is driven off or oxidized to form a metal oxide species." This use of the metal alkoxide as an extremely pure source of the metal is also one of the motives for using it to wash coat monolith honeycombs, as described in U.S. Pat. No. 3,873,469, cited hereinabove. Still another embodiment of the invention described in U.S. Pat. No. 4,400,306 consists of "choosing particular alkoxy derivatives of reducible metal ions" so that an in situ reduction of the metal can be effected (column 3, lines 57-59).

The metal alkoxide impregantion step can also be repeated to increase the amount of metal (or metal oxide) deposited within the support. After the impregnation of one metal alkoxide catalyst component, additional catalyst components can be added in the form of metal alkoxide solutions or solutions of other catalyst component compounds. Catalysts prepared in this way are suitable for fixed-bed or fluid-bed catalytic processes, particularly for oxidation processes like the conversion of $C_4$ hydrocarbons to maleic anhydride (cf. U.S. Pat. No. 4,455,434).

To summarize, metal alkoxides have been used in the prior art for the manufacture of solid catalysts for the following distinct purposes and with the following specific characteristics:

1. to wash coat a monolithic honeycomb, to give the inert refractory substrate higher surface area and porosity for subsequent metal impregnation (U.S. Pat. Nos. 3,873,469; 4,076,792);

2. to bring alkali metal ions in a water-free system to catalysts to neutralize the unwanted strong acidity of the catalysts (Paper of Hombek et al., 1978, supra);

3. to impregnate vanadium alkoxides on silica or alumina to prepare supported vanadium catalysts. The alkoxide is used as a water-free medium to prevent side effects to the catalyst support which would otherwise result from using an aqueous solution of a vanadium salt (Glinski and Kijenski, 1982, supra);

4. use of the specific alkoxide of the catalytically active metal, as alkoxides are generally purer than the corresponding metal salts, hence trace impurities can be avoided if metal alkoxides are used instead of metal salt solutions (U.S. Pat. Nos. 4,400,306 and 4,455,434).

Catalytic metals play an important role in heterogeneous catalysis. The catalytic metals typically are employed on various support materials, as only the surface of a metal particle can participate in a catalytic process. Many people have proposed various solutions to the long-standing problem of how to disperse catalytic metals more efficiently on the surface of a support material. However, the art has not recognized the present invention as being an improved solution to the problem.

SUMMARY OF THE INVENTION

In one aspect, the present invention is an improved catalyst composition comprising a catalytic metal on an alkoxide-modified support.

In another aspect, the invention is a method of increasing the catalytic activity of a catalytic metal, the method comprising supporting the catalytic metal on a support prepared by contacting a metal alkoxide with a core support, then calcining the mixture of the metal alkoxide and the core support thereby leaving a coating on the core support, the coating comprising the metal oxide derived from the calcination of the metal alkoxide.

In yet another aspect, the present invention is the use of a catalyst composition of the present invention in a process for producing methane in an improved yield by contacting carbon monoxide and hydrogen under reaction conditions. Other inventive processes include carbonylation, the selective hydrogenation of acetylene, and olefin metathesis.

Surprisingly, the supported catalyst composition of the present invention exhibits increased catalytic activity compared to supports not treated by the method of this invention. Thus, the catalyst composition of the present invention is useful in many catalytic processes in which enhanced activity of a supported metal catalyst is desirable. For example, the proper catalyst composition can be employed in the production of methane in improved yields. Other exemplary uses of the catalyst composition are described herein.

DETAILED DESCRIPTION OF THE INVENTION

Figure 1:
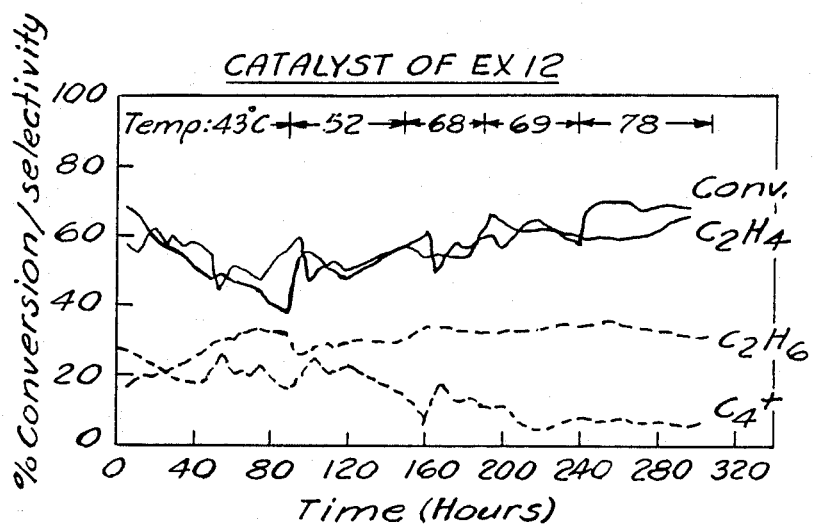
FIGS. 1–4 graphically depict the results of Example 12 and Comparative Experiment 12, relating to an acetylene hydrogenation process using a catalyst of the present invention (FIGS. 1 and 2) and a commercial catalyst (FIGS. 3 and 4).

The catalyst composition of the present invention has two required components: a catalytic metal; and an alkoxide-modified support. For the purposes of the present invention, the term "alkoxide-modified support" means a material prepared by depositing a thin layer of a metal alkoxide on a core support material and then converting the metal alkoxide to the oxide of said metal. Additionally, the term "catalytic metal" refers to any metal-containing compound, complex or other entity which acts as a catalyst.

The alkoxide-modified support comprises a core support material having on its outer surface a thin layer of a metal oxide produced from a precursor metal alkoxide. The core support material can be any material, such as a refractory oxide, which will not decompose or melt when subjected to calcination. Examples of typical core support materials include alumina, zirconia, boria, thoria, magnesia, titania, tantala, chromia, silica, kieselguhr and mixtures of these materials. The aluminas and silicas are preferred in view of their low cost. The core support material typically has a surface area which is greater than about 5 m$^2$/g, preferably about 10 to 500 m$^2$/g, more preferably 20 to 200 m$^2$/g, and most preferably over 100 m$^2$/g prior to the deposition of the metal alkoxide salt precursor. These surface areas are as measured by the Brunauer-Emmett-Teller (BET) method. The BET method is described by R. B. Anderson, *Experimental Methods in Catalytic Research*, pp. 48–66, Academic Press, 1968.

The precursor metal alkoxide can be the alkoxide of almost any metal so long as said metal alkoxide will thermally decompose to form a metal oxide. For example, the metal of the metal alkoxide can be a metal of group IIA. Examples of preferred metals for use in the precursor metal alkoxide include the metals of Groups IIIA, IVA, IVB and VB of the Periodic Table of the elements. Examples of typical precursor metal alkoxides include $Al(OCH(CH_2CH_3)(CH_3))_3$, $Ti(OCH(CH_3)_2)_4$, $Ta(OCH(CH_3)_2)_5$, $Si(OC_2H_5)_4$, $Nb_2(OC_2H_5)_{10}$, $Ta_2(OC_2H_5)_{10}$, $Si(OC_4H_9)_4$, $Al(OC_5H_{11})_3$, and the like. Typically, the alkoxide moiety has from 1 to about 10 carbon atoms, preferably from about 2 to about 4 carbon atoms. Mixtures of metal alkoxides can be employed. Typically, the metal of the metal alkoxide is not a catalyst for the reaction in which the catalyst composition will be employed.

The alkoxide-modified support is prepared by techniques known in the art, e.g., incipient wetness impregnation techniques, etc. Metal oxide precursors are deposited on the selected core support material followed by conversion into the oxide form by calcination. The alkoxide-modified support is prepared by impregnating the desired core support material with a solution of an alkoxide precursor of the desired metal oxide. The solution used in impregnating the core support material preferably is organic, the only requirement being that an adequate amount of precursor compound for the selected metal oxide is soluble in the solvent used in preparing the impregnating solution. Hydrocarbon or alcohol solutions, preferably hexane solutions, are normally used for convenience. When using the impregnation technique the metal alkoxide impregnating solution is contacted with the core support material for a time sufficient to deposit the metal alkoxide precursor material onto the carrier either by selective adsorption or, alternatively, the excess solvent may be evaporated during drying leaving behind the precursor metal alkoxide. Advantageously, the incipient wetness technique may be used whereby just enough of a precursor metal alkoxide solution is added to dampen and fill the pores of the powder of the above-recited core support material.

The composite thus prepared by any of the above-recited techniques, or by any other technique known in the art, is dried, typically at a temperature of from 50° C. to 300° C., to remove the excess solvent. The solvent can be removed in vacuo. The dried metal alkoxide can then be converted into the oxide form by exposure at temperatures typically of from 150° C. to 800° C., preferably 300° C. to 700° C. in an atmosphere such as $O_2$, air, He, Ar or combinations thereof. This exposure is for a time sufficient to convert essentially all of the metal alkoxide precursor into metal oxide. The calcination is useful to decompose the metal precursor to the oxide form.

The catalytic metal can be any metal or metal compound having catalytic activity. Typical catalytic metals include the transition metals. Examples of preferred catalytic metals include the metals of Group VIII of the Periodic Table of the elements, i.e., iron, ruthenium, osmium, cobalt, rhodium, iridium, nickel, palladium and platinum, and the metals of Group VIIB, e.g., rhenium. The catalytic metal is deposited on the alkoxide-modified support via methods known in the art such as, for example, impregnation of the alkoxide-modified support with a salt of the catalytic metal. The salt of the catalytic metal is converted to the metal by exposing the salt to a reducing atmosphere via methods known in the art. It is preferred to reduce the salt of the catalytic metal in situ, i.e., while the salt is in the reaction vessel.

The precursor metal alkoxide is employed in an amount sufficient to result in a finished alkoxide-modified support which, after calcination, can be employed with a catalytic metal to form a composite catalyst composition having improved activity, which may be evidenced, e.g., by increased conversion or lifetime. Typically, the support has up to about a molecular monolayer of the metal oxide, formed from the metal alkoxide, covering the entire outer surface of the core support material. If desired, more than a molecular monolayer of the metal oxide from the metal alkoxide can be employed. Typically, the catalytic metal is employed in a catalytic amount. Preferably, the finished catalyst of the present invention will have a composition as follows: from about 0.01 to about 20 weight percent catalytic metal; from about 0.1 to about 50 weight percent of metal oxide from alkoxide precursor; and the remainder being core support material. More preferably, the finished catalyst of the present invention will have a composition as follows: from about 0.02 to about 10 weight percent catalytic metal; from about 1 to about 5 weight percent metal oxide from alkoxide precursor; and the remainder being core support material.

A. Methanation

The catalyst composition of the present invention is useful in many applications in which enhanced activity of a supported catalytic metal is desirable. The production of methane from CO and $H_2$ is an example of a preferred use of the catalyst composition of the present invention. The art contains many examples of metals known to be useful in reacting carbon monoxide with hydrogen to produce a variety of compounds, including hydrocarbons and oxygenated compounds. These metals include, among others, Mo, W, Rh, Ru, Re, Pd, Ni, Co, and Fe. In what has come to be called the Fischer-Tropsch Synthesis, carbon monoxide and hydrogen are reacted over a metal catalyst to produce saturated and unsaturated hydrocarbons and oxygenated compounds containing from 1 to as many as 1000 carbon atoms. The hydrocarbons can be aliphatic, alicyclic, or aromatic. Commercial utilization of this synthesis prior to 1950 was accomplished largely in Germany and is summarized in Storch, Columbic, and Anderson: *The Fischer-Tropsch and Related Synthesis*, John Wiley and Sons, New York, 1951.

The major disadvantage in the prior art processes and catalysts is that most of them are not capable of selectively producing methane. Surprisingly, at least one catalyst of the present invention may be used to produce methane selectively by contacting carbon monoxide and hydrogen in the presence of said catalyst under reaction conditions.

The carbon monoxide required for the process can be obtained from any carbon source, such as from the degradation of coal. The molar ratio of hydrogen to carbon monoxide ranges generally from at least about 0.1 to about 10, and preferably is from about 1 to about 3. Process reaction conditions can vary over a rather wide range. The pressure can vary from at least about 1 psig up to about 1500 psig. Atmospheric pressure is preferred for convenience. The reaction temperature typically ranges from at least about 200° C. to about 600° C. and preferably is from about 200° C. to about 300° C. Ruthenium is the preferred catalytic metal for use in the production of methane via the process of the present invention.

B. Olefin Metathesis

The disproportionation, or metathesis, of olefins is another example of an advantageous use of the supported catalyst composition of the present invention. In a typical olefin metathesis process an olefin of at least 3 carbon atoms is converted into a mixture of new products comprising olefins of both higher and lower molecular weight compared to the olefin fed. Olefin metathesis was discovered in the early 1960s. The metathesis reaction is well-known, as is evidenced by the numerous publications which are reviewed in *Catalysis*, Vol. 4, pp. 101-130, 1980, which article, and the articles cited therein, are incorporated herein by reference. A review of the prior art indicates that it would be desirable to have a catalyst having a longer lifetime or which would require fewer regenerations per unit time. Surprisingly, at least one catalyst of the present invention may be employed in the metathesis of olefins for increased lengths of time while maintaining an acceptable rate of olefin conversion.

The olefin metathesis process of the present invention involves contacting at least one alkene with a catalyst of the present invention under reaction conditions such that there is formed at least one product of olefin metathesis, i.e., at least one alkene having a molecular weight which is different than the molecular weight of the alkene fed to the reactor.

Alkenes which are subject to disproportionation according to the process of the present invention include acyclic alkenes having at least 3 carbon atoms, and their aryl derivatives and mixtures thereof. Preferred are alkenes having from 3 to about 30 carbon atoms and mixtures thereof. More preferred are mono-1- and 2-alkenes, such as, for example, propene, butene-1, and mixtures of these alkenes, such as, for example, a mixture of butene-1 and butene-2. Most preferably, the process of the present invention is applied to butene-1 or a mixture of butene-1 and butene-2. Optionally, an inert material may be included in the alkene fed to the reactor. Examples of inert materials include inert gases, such as helium, and saturated hydrocarbons, such as hexane, cyclohexane, and the like.

Catalysts suitable for use in the olefin metathesis process of the present invention are those materials which catalyze the olefin metathesis reaction; typically, the catalyst is a conventional catalytic material on an alkoxide-modified support. Examples of said conventional catalysts include materials which contain catalytic metals such as rhenium, molybdenum or tungsten, and which optionally include a promoter, such as tetramethyltin or tetrabutyltin. Preferred catalysts comprise rhenium or a rhenium compound or complex. Rhenium oxides are preferred for use in the catalysts of the process of the present invention. It is especially preferred to employ from about 1 to about 8 weight percent catalytic metal in the composite catalyst for olefin metathesis.

The composite olefin metathesis catalyst is prepared by suitable known methods of applying a catalytic material to a support, such as impregnation or coprecipitation, with impregnation being preferred. Catalytic metal oxides or compounds convertible to catalytic metal oxides by calcination preferably are employed in the catalyst preparation.

After the catalytic metal oxide, or compound which may be converted to a catalytic metal oxide by calcination, is associated with the alkoxide-modified support, the composite is subjected to a calcination or activation step before being utilized in the olefin conversion process. The activation technique comprises heating at elevated temperatures in the presence of a suitable flowing gas. Air is a preferred activation gas, although other gases, for example, inert gases such as nitrogen or the noble gases, may be used, provided that at least part of the catalytic metal present in the catalyst composition is in the oxide form at the completion of the activation. The catalysts are subjected to a temperature which is generally in the range of 300° C. to 700° C. for about 0.5 to 20 hours or longer. Generally, longer activation periods are used with lower temperatures, and shorter activation periods are used with higher temperatures. In some instances, the catalyst may be heated serially in more than one gas.

The activated catalyst may be used, without regeneration, for runs of up to several days or more, and may be regenerated. The regeneration is accomplished by suitable methods for regenerating oxide catalysts and may comprise the same steps used in the activation procedure.

The reactor employed in the olefin metathesis process of the present invention can be of any known design. The reactor is operated so as to disproportionate the alkenes in the feed stream. Accordingly, the reactor may be operated under any conditions, at which disproportionation is achieved. Typically, the operating temperature in the reactor ranges from about −50° C. to about 300° C., and preferably will be from about 0° C. to about 150° C. The pressure in the reactor typically will be from about zero to about 1000 psig and preferably will be from about 50 to about 300 psig. Higher or lower temperatures and pressures may be employed; however, beyond the lower end of the range the reaction will proceed slowly, if at all, and beyond the higher end of the range, undesirable side reactions and coke formation may occur. Additionally, it will probably be more expensive to operate outside the ranges given.

For the purposes of the metathesis process of the present invention, the term conversion refers to the elimination of the alkenes in the feed stream from the reaction mixture. For example, in the practice of this invention, butene-1 may be converted to ethylene and hexene-3 under the proper conditions. For the purposes of the present invention, the term selectivity refers to the percentage of the converted feed which goes to the desired major products The concept of simultaneous high selectivity and high conversion may be expressed conveniently in terms of yield. For the purposes of the present invention, the term "yield" refers to the numerical product of conversion and selectivity. For example, a process according to the present invention operating at a conversion of 0.75 and a selectivity of 0.90 would have a yield of 0.675, which is the numerical product of 0.75 and 0.90.

C. Carbonylation

The carbonylation of haloalkenes is a further example of an advantageous use of the supported catalyst composition of the present invention. The carbonylation reaction of the present invention is a process for the preparation of α-substituted acrylate esters which involves contacting a haloalkene with carbon monoxide and an alcohol or an ether in the presence of a catalyst of the present invention under reaction conditions such that an α-substituted acrylate ester is prepared.

The preparation of acrylate esters by contacting haloalkenes, carbon monoxide, and an alcohol or ester in the presence of a heterogeneous catalyst is generally known. For example, see U.S. Pat. No. 4,480,121, which is incorporated herein by reference for a description of reactants and reaction conditions employed in the preparation of acrylate esters. The haloalkenes useful in this invention include any halogenated olefinic compound wherein the halogen is substituted on an olefinic carbon atom, wherein such carbon atom is further substituted with a $C_{1-10}$ alkyl, $C_{3-10}$ cycloalkyl, $C_{6-10}$ aryl, $C_{7-10}$ alkaryl, $C_{7-10}$ aralkyl, cyano, or trihalomethyl group. The haloalkene preferably is vaporizable under the reaction conditions. Olefinic carbon atoms means herein a carbon atom which is doubly bonded to another carbon atom. Haloalkenes useful in this invention include those which correspond to the formula

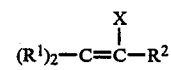

wherein
$R^1$ is H, $C_{7-10}$ aryl, $C_{1-10}$ alkyl, $C_{3-10}$ cycloalkyl, $C_{7-10}$ alkaryl, $C_{7-10}$ aralkyl, substituted $C_{1-10}$ alkyl, substituted $C_{6-10}$ aryl, substituted $C_{3-10}$ cycloalkyl, substituted $C_{7-10}$ alkaryl or substituted $C_{7-10}$ aralkyl, wherein the substituent is a nitro, cyano, carbonyloxyhydrocarbyl, formyl, amino, hydroxyl, amido or halo group;
$R^2$ is $C_{1-10}$ alkyl, $C_{3-10}$ cycloalkyl, $C_{6-10}$ aryl, $C_{7-10}$ alkaryl, $C_{7-10}$ aralkyl, cyano or trihalomethyl; and X is halogen.

Examples of preferred haloalkenes useful in this invention include 2-chloropropene, 2-bromopropene, 2-chlorobutene, 2-bromobutene, 2-chloropentene, 3-chloropentene, 2-bromopentene, 3-bromopentene, 2-chlorohexene, 3-chlorohexene, 2-bromohexene, 3-bromohexene, and the like. More preferred haloalkenes include 2-chloropropene, 2-chlorobutene, 2-chloropentene, and 2-chlorohexene. A most preferred haloalkene is 2-chloropropene.

Alcohols useful in this invention include those which are vaporizable under reaction conditions and which will react under the reaction conditions to esterify the carbonylated haloalkene so as to prepare an α-substituted acrylate ester. Preferred alcohols include those which correspond to the formula, $R^3OH$, wherein $R^3$ is $C_{1-10}$ alkyl, $C_{3-10}$ cycloalkyl, $C_{6-10}$ aryl, $C_{7-10}$ alkaryl, or $C_{7-10}$ aralkyl. Examples of alcohols useful in this invention include methanol, ethanol, propanol, butanol, hexanol, heptanol, octanol, nonanol, decanol, cyclopropanol, cyclobutanol, cyclopentanol, cyclohexanol, cycloheptanol, cyclooctanol, phenol, benzyl alcohol, and the like. Preferred alcohols are methanol, ethanol, propanol, butanol, and pentanol. Methanol is the most preferred alcohol.

Ethers useful in this invention include those which are vaporizable under reaction conditions and which will react under the reaction conditions to esterify the carbonylate haloalkene so as to prepare an α-substituted acrylate ester. Among classes of ethers useful in this invention are the dihydrocarbyl ethers and cyclic ethers. Preferred dihydrocarbyl ethers include those which correspond to the formula $R^3$—O—$R^3$ wherein $R^3$ is as defined hereinbefore. Examples of dihydrocarbyl ethers useful in this invention are dimethyl ether, diethyl ether, dipropyl ether, dibutyl ether, dipentyl ether, diphenyl ether, dibenzyl ether and the like. Preferred ethers are dimethyl ether, diethyl ether and dipropyl ether; with dimethyl ether being most preferred. Unsymmetrical dihydrocarbyl ethers such as methyl ethyl ether, can be used in this invention although the symmetrical ethers are preferred. Preferable cyclic ethers useful in this process include those which correspond to the formula

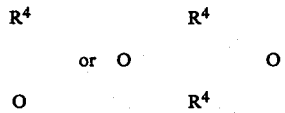

wherein $R^4$ is a hydrocarbylene radical. The dihydrocarbyl ethers are preferred over the cyclic ethers. Cyclic ethers useful in this invention include dioxane, tetrahydrofuran and the like.

The product of the carbonylation process of the present invention is an acrylate ester. Preferred α-substituted acrylate esters include those which correspond to the formula

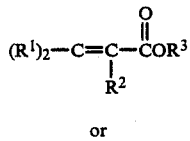

or

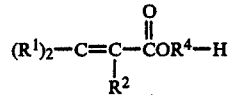

wherein $R^1$, $R^2$, $R^3$ and $R^4$ are as hereinbefore defined.

Examples of acrylate esters prepared by this process include methyl methacrylate, methyl 2-methyl-2-butenoate, methyl 2-methyl-2-pentenoate, ethyl methacrylate, ethyl 2-methyl-2-butenoate, ethyl 2-methyl-2-pentenoate, propyl methacrylate, propyl 2-methyl-2-butenoate, propyl 2-methyl-2-pentenoate, butyl methacrylate, butyl 2-methyl-2-butenoate, butyl 2-methyl-2-butenoate, pentyl methacrylate, pentyl 2-methyl-2-butenoate, and pentyl 2-methyl-pentenoate. Preferred acrylate esters include methyl methacrylate, ethyl methacrylate, propyl methacrylate, butyl methacrylate, and pentyl methacrylate, more preferred acrylate esters include methyl methacrylate, ethyl methacrylate, and propyl methacrylate, with methyl methacrylate being most preferred.

A co-product of this invention is a hydrocarbyl halide. This halide is the reaction product of an alcohol or an ether and the halogen abstracted from the haloalkene during the carbonylation and esterification process of this invention. The excess alcohol or ether functions as the halogen acceptor for this reaction thereby reducing the concentration of hydrogen halide in the reactor and preventing corrosion. Furthermore, the preparation of an alkyl halide allows the recovery of the halogen in a valuable form. Hydrocarbyl halides prepared in this invention include those which correspond to the formula, $R^3$—X or $R^4H$—X, wherein $R^3$ and $R^4$ are as hereinbefore defined.

Tertiary amines may be used as hydrogen halide acceptors. When tertiary amines are used as acid acceptors, by-products of the process are the quaternary ammonium halides. The use of excess alcohols or ethers to serve as the halogen acceptor is preferred over the use of the tertiary amines in this invention.

Examples of haloalkanes prepared by this process include chloromethane, chloroethane, chloropropane, chlorobutane, chloropentane, chlorohexane, chloroheptane, chlorooctane, chlorononane, chlorodecane, chlorocyclopropane, chlorocyclobutane, chlorocyclopentane, chlorocyclohexane, chlorobenzene, chloromethylbenzene, bromomethane, bromoethane, bromopropane, bromobutane, bromopentane, bromohexane, bromoheptane, bromooctane, bromononane, bromodecane, bromocyclopropane, bromocyclobutane, bromocyclopentane, bromocyclohexane, bromobenzene, and bromomethylbenzene. Examples of more preferred haloalkanes include chloromethane, chloroethane, chloropropane, chlorobutane, chloropentane, chlorohexane, chloroheptane, chlorooctane, chlorononane, chlorodecane, chlorocyclopropane, chlorocyclobutane, chlorocyclopentane, chlorocyclohexane, chlorobenzene, and chloromethylbenzene. Even more preferred haloalkanes include chloromethane, chloroethane, chloropropane, chlorobutane and chloropentane, with chloromethane being most preferred.

In the process of this invention, the haloalkene starting material is carbonylated by the insertion of carbon monoxide onto an olefinic carbon atom, and the carbon atom on the carbon monoxide moiety inserted is transesterified with the alcohol or ether. This process can be best illustrated by the following equations,

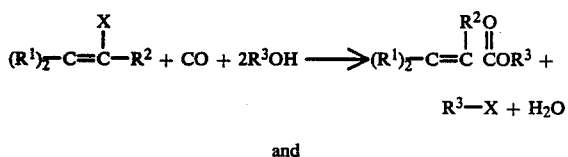

and

wherein $R^1$, $R^2$, $R^3$, and X are as hereinbefore defined.

In the hereinbefore defined formulas, $R^1$ is preferably hydrogen or $C_{1-10}$ alkyl. $R^1$ is more preferably hydrogen or $C_{1-5}$ alkyl and most preferably hydrogen. $R^2$ is preferably $C_{1-10}$ alkyl. $R^2$ is more preferably $C_{1-5}$ alkyl and most preferably methyl. $R^3$ is preferably $C_{1-10}$ alkyl, $R^3$ is more preferably $C_{1-5}$ alkyl and most preferably methyl. $R^4$ is preferably $C_{2-10}$ alkylene and more preferably $C_{2-5}$ alkylene. X is preferably chlorine or bromine and most preferably chlorine.

For the purposes of the present invention, the term "hydrocarbyl" means an organic radical containing carbon and hydrogen atoms. The term hydrocarbyl includes the following organic radicals: alkyl, alkenyl, alkynyl, cycloalkyl, cycloalkenyl, aryl, aliphatic and cycloaliphatic aralkyl and alkaryl. Aliphatic refers herein to straight- and branched-, and saturated and unsaturated, hydrocarbon chains, that is, alkyl, alkenyl or alkynyl. Cycloaliphatic refers herein to saturated and unsaturated cyclic hydrocarbons, that is, cycloalkenyl and cycloalkyl. The term aryl refers herein to biaryl, biphenylyl, phenyl, naphthyl, phenanthranyl, anthranyl and two aryl groups bridged by an alkylene group. Alkaryl refers herein to an alkyl-, alkenyl- or alkynyl-substituted aryl substituent wherein aryl is as defined hereinbefore. Aralkyl means herein an alkyl, alkenyl or alkynyl group substituted with an aryl group, wherein aryl is as defined hereinbefore. $C_{1-20}$ alkyl includes straight- and branched-chain methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl and eicosyl groups. $C_{1-5}$ alkyl includes methyl, ethyl, propyl, butyl and pentyl.

Cycloalkyl refers to alkyl groups containing one, two, three or more cyclic rings. Cycloalkenyl refers to mono-, di- and polycyclic groups containing one or more double bonds. Cycloalkenyl also refers to cycloalkenyl groups wherein two or more double bonds are present.

The catalytic metals useful in the carbonylation process are palladium, platinum, rhodium, ruthenium, nickel and mixtures thereof. Preferred catalytic metals are palladium and nickel, with palladium being most preferred.

The carbonylation catalyst comprises an alkoxide-modified support with a sufficient amount of one of the hereinbefore described metals loaded thereon to give the desired catalyst productivity for the claimed process. The catalyst preferably comprises an alkoxide-modified support with between about 0.1 and 10 percent by weight of the hereinbefore described metal, more preferably between about 1 and 10 percent by weight, and most preferably between about 3 and 7 percent.

The carbonylation catalysts preferably are prepared by incipient wetness techniques, which are well-known in the art. In particular, a salt of the metals described hereinbefore is dissolved in water or an aromatic hydrocarbon and thereafter contacted with the particular support. Examples of salts which can be used include metal acetates, metal halides, metal nitrates, and the like.

A particularly preferred catalyst comprises palladium deposited onto an alkoxide-modified support wherein the core support is α-alumina and the metal of the metal alkoxide is alumina. Preferred supports have a surface area from about 10 m²/g to about 350 m²/g and more preferably from about 100 m²/g to about 300 m²/g.

In a preferred carbonylation catalyst preparation procedure, a previously prepared alkoxide-modified support and an aqueous hydrochloric acid solution of a palladium salt having a pH of 3.0 or less are contacted at elevated temperatures. Preferably, the support is heated to a temperature from about 75° C. to about 150° C. and the aqueous hydrochloric acid solution is heated to a temperature of from about 50° C. to about 95° C. at the time the support and solution are contacted. Only sufficient solution so as to result in incipient wetness of the substrate is employed. Accordingly, the volume and metal concentration of the aqueous solution are adjusted to provide sufficient metal loadings and sufficient volume of liquid to completely wet the support, but not provide more liquid than can be absorbed by the support. Preferably, the aqueous solution has a pH of 2.0 or less.

After impregnation with the palladium solution, the catalyst preferably is dried in flowing air at elevated temperatures up to about 300° C. for several hours. Reduction may then occur employing hydrogen under the temperatures and conditions described hereinafter.

The carbonylation catalyst preferably is activated by passing hydrogen gas over the impregnated catalytic support at a temperature of between about 150° C. and 350° C., for a period of time to reduce a significant amount of the metal salt impregnated on the support. Preferably, the hydrogen gas is passed over the support at a temperature of between about 225° C. and 300° C., with between about 240° C. and 280° C. being most preferred. It is preferable to flow hydrogen gas over the catalyst for a time period of between about 1 and 10 hours.

It is believed that during the activation procedure the metal is reduced to the zero valence state, which is believed to be the catalytic species.

In general, the support is impregnated with a sufficient amount of metal so as to create a carbonylation catalyst which is active under the reaction conditions. The amount of active metal on the carrier can be between about 0.01 and 99 percent by weight of the support. Preferably, the catalyst contains between about 0.1 and 10 percent by weight of active metal. Even more preferably, the catalyst contains between about 1 and 10 percent by weight of the active metal, with between about 3 and 7 percent by weight of the active metal on the catalyst being most preferred.

It has been discovered that the presence of an alcohol or ether in the reactants results in significant increases in the productivity of the catalyst for the α-substituted acrylate ester. The mole ratio of the alcohol to the haloalkene in the feed composition has a significant effect on the productivities, conversions and selectivities. The productivities, conversions and selectivities are enhanced as the equivalent ratio of alcohol or ether to haloalkene increases from 1:1 to 2:1. At 2:1 the productivities, conversions and selectivities are optimized. The ratio of alcohol or ether to olefin can be any ratio which gives a desired conversion and selectivity. Preferably, the equivalent ratio of alcohol or ether to haloalkene is 1.5:1 or above. More preferably the alcohol or ether to haloalkene ratio is 2.0:1 or greater. An equivalent with respect to the alcohol or ether, refers herein to that amount of alcohol or ether which provides one mole of hydrocarbyl radicals. In particular, one mole of a dihydrocarbyl ether provides two equivalents of hydrocarbyl radicals, while one of an alcohol provides one equivalent of hydrocarbyl radicals.

At least a stoichiometric ratio of carbon monoxide to haloalkene is needed for this process to give good selectivities and conversions.

The temperature used for the carbonylation process has a significant effect on the conversions, selectivities, catalyst productivity and catalyst lifetime. In practice, any temperature at which the desired conversions, selectivites, productivity, and catalyst lifetime are achieved can be used. Preferable reaction temperatures are between about 125° C. and 250° C., with 170° C. to 240° C. being more preferred. In general, above 250° C. the rate of reaction significantly decreases. Below 125° C., the reaction rate is extremely slow.

The reaction pressure also has a significant effect on the selectivities, conversions, catalyst productivity and catalyst lifetime. Any reaction pressure which gives the desired selectivities, conversions, catalyst productivity and catalyst lifetime can be used. Preferred pressures are between about 100 and 800 psi, with between about 300 and 600 psi being most preferred. Above 800 psi the rate of reaction drops dramatically and below 100 psi the selectivity of the reaction is ver poor.

The flow rate over the catalyst can be any flow rate which gives the desired conversions and selectivities. In practice, the flow rate of carbon monoxide is between about 15 gas volumes of carbon monoxide per volume of catalyst per hour and 1500 gas volumes of carbon monoxide per volume of catalyst per hour. Preferably, the flow rate is between about 100 and 200 gas volumes of carbon monoxide per volume of catalyst per hour.

It is preferable that the alcohol or ether and haloalkene be vaporized by preheating before contacting them with the carbon monoxide in the presence of the catalyst, i.e., it is preferred to operate in the vapor phase. The combined alcohol or ether and haloalkene feed to the preheater is preferably between about 0.1 and 10 liquid volumes per volume of catalyst per hour. More preferably, the feed rate is between about 0.5 and 1.5 liquid volumes of haloalkene and alcohol or ether per volume of catalyst per hour.

This process can be performed in a batch or continuous mode. Furthermore, the catalyst can be used as a fixed bed catalyst or in a fluid bed. It is preferred to use a continuous mode with a fixed bed catalyst.

In one preferred embodiment, methylmethacrylate is prepared by contacting 2-chloropropene, carbon monoxide and methanol, or dimethyl ether in the vapor phase over a catalyst which comprises palladium on $AlO_x$/alumina wherein the concentration of palladium on the support is between about 1 and 7 percent by weight. In this embodiment, the catalyst is prepared by impregnating palladium chloride onto the support. The catalyst is activated by passing hydrogen gas over the supported palladium chloride at a temperature of between about 240° C. and 280° C. for a period of between 1 and 3 hours. In this embodiment, the contacting of the reactants takes place at between about 170° C. and 240° C. under a pressure of 300 to 600 psi.

The carbonylation process of this invention results in a process for the preparation of acrylate esters wherein the catalyst exhibits long lifetimes, with good productivities and selectivities. The process of this invention results in catalyst productivities of at least about 0.06 g of product per gram of catalyst per hour, under more preferred conditions a productivity of at least about 0.10 g of product per gram of catalyst per hour, and under most preferred conditions at least about 0.25 g of product per gram of catalyst per hour. The process of this invention results in selectivities toward α-unsubstituted acrylate ester of 70 percent or greater, under preferred conditions, of 80 percent or greater, and under most preferred conditions 85 percent or greater.

Referring to the carbonylation reaction, conversion refers to the amount of haloalkane converted to products, and selectivities refer to the percentage of acrylate esters in the products prepared.

D. Hydrogenation

The selective hydrogenation of alkynes amidst major proportions of alkenes is a known reaction. For example, the manufacture of unsaturated hydrocarbons usually involves cracking higher hydrocarbons and produces a crude product containing, as impurities, hydrocarbons that are more unsaturated than the desired product but which are very difficult to separate by fractionation. A common example is the manufacture of ethylene in which acetylene is a contaminant. In a similar way, the formation of propylene is accompanied by hydrocarbons of the empirical formula $C_3H_4$ (e.g., methyl acetylene and allene), and the formation of butadiene by vinyl acetylene. The content of the undesired hydrocarbons depends upon the severity of the conversion treatment, but is always too low to permit their separation economically by conventional means such as distillation. However, such highly unsaturated hydrocarbons can be removed by hydrogenation using process conditions and a carefully formulated catalyst such that no significant hydrogenation of the desired hydrocarbon takes place.

U.S. Pat. No. 4,347,392 discloses a hydrogenation catalyst which is palladium on alumina with the average size of the palladium crystallites being at least 50 angstroms. However, the preparation of said catalyst is disadvantageous in that the catalyst must be subjected to heat activation at a temperature of 600° C. to 1100° C.

U.S. Pat. No. 4,126,645 discloses a hydrogenation catalyst which comprises palladium supported on particulate alumina, the catalyst having a surface area in the range of 5 to 50 $m^2/g$, a helium density of under 5 $g/cm^3$, a mercury density of under 1.4 $g/cm^3$ and a pore volume of at least 0.4 $cm^3/g$, at least 0.1 $cm^3/g$ of which is in pores of radius over 300 angstrom units, the palladium being present mainly in the region of the catalyst particles not more than 150 microns beneath their geometric surface. The alumina can be a coating on the surface of a honeycomb.

U.S. Pat. No. 4,410,455 discloses a hydrogenation catalyst support prepared by applying a specified calcium aluminate material to a honeycomb.

It would be desirable to have an improved catalyst for the selective hydrogenation of alkynes and dienes amidst a major proportion of alkenes. Surprisingly, the catalyst of the present invention exhibits improved selectivity and/or activity relative to commercially available catalysts for the hydrogenation of acetylenic impurities.

The hydrogenation process of the present invention is a process for hydrogenating a hydrocarbon composition comprising at least one alkene and at least one alkyne, the process comprising contacting the hydrocarbon composition with a catalyst of the present invention under reaction conditions to selectively hydrogenate the alkyne without substantially hydrogenating the alkene.

Two general types of gaseous selective hydrogenation processes for purifying unsaturated hydrocarbons have come into use. One, known as "front-end" hydrogenation, involves passing the crude gas from the initial cracking step, after removal of steam and condensible organic matter, over a hydrogenation catalyst. The crude gas normally contains a relatively large amount of hydrogen, far in excess of that required to hydrogenate a substantial part of the olefin present. Despite this hydrogen excess, operation with sufficient selectivity to give olefins of polymerisation quality is well established and catalyst lives of many years are obtained. In the other type, known as "tail-end" hydrogenation, the crude gas is fractionated and the resulting product streams are reacted with hydrogen in slight excess over the quantity required for hydrogenation of the highly unsaturated hydrocarbons present. The tail-end hydrogenation is less critical than front-end hydrogenation in that at the low hydrogen excess a runaway reaction is not possible; however, there is a greater tendency to deactivation of the catalyst and formation of polymers from the highly unsaturated hydrocarbons may occur as an alternative to the hydrogenation thereof. Consequently periodic regeneration of the catalyst is required.

When the process is a "front-end" hydrogenation, the temperature is suitably up to 250° C., for example 60° C.–150° C.; the pressure is suitably in the range 1–70 atm, for example 8–40 atm; and the space velocity is suitably in the range 100–20000, for example 5000–15000 hour$^{-1}$, that is, liters per liter of catalyst-filled space per hour, calculated for 20° C., 1 atm pressure. The volume percentage composition of the gas fed to the catalyst is suitably as follows for a process producing ethylene and/or propylene as main products:

ethylene or propylene: 10–45
propylene or ethylene: up to 20 (when both are present)
higher hydrocarbons: up to 2
acetylene and/or $C_3H_4$: 0.01 to 2
hydrogen: 5–40
unreactive gases (e.g., alkanes, nitrogen): balance For long catalyst life without regeneration the hydrogen content is preferably at least 5 times by volume as much as the content of acetylene and $C_3H_4$.

When the process is a tail-end hydrogenation the temperature is suitably in the range 40° C.–150° C.; the pressure is suitably in the range 1–70 atm, for example 8–40 atm; and the space velocity is suitably in the range 500–7000 hour$^{-1}$, that is, liters of gas per liter of catalyst-filled space per hour. The hydrogen content should be at least sufficient to hydrogenate to mono-olefin all the highly unsaturated hydrocarbons present and is preferably from about 1.0 to about 1.5 times that content for acetylene. The life of the catalyst between regenerations is longer the higher the hydrogen content of the gas, but this advantage is counter-balanced by the expense of separating and recycling greater quantities of saturated hydrocarbon. The gas passed over the catalyst typically contains up to about 6 percent (for example 0.1 to 3.0 percent) of highly unsaturated hydrocarbons and at least 50 percent, sometimes over 95 percent, of the desired mono-olefin or conjugated diolefin.

When the process is a tail-end liquid-phase selective hydrogenation the temperature is typically 0° C.–50° C., the pressure up to about 50 atm, and the space velocity typically 5–40 kg per hour per liter of catalyst-filled space. The liquid hydrocarbon suitably trickles downwards over the catalyst in a substantially stationary hydrogen atmosphere.

Whichever type of hydrogenation is used, it appears to be advantageous to have present a small quantity of carbon monoxide. In a front-end hydrogenation the proportion of carbon monoxide is suitably 0.03 to 3.0 percent v/v of the total gas mixture. Such a content commonly enters in as a by-product of the initial cracking reaction.

In a tail-end hydrogenation the proportion is suitably in the range 4.0 to 500 ppm v/v; it may be added deliberately if fractionation of the crude gas has removed it or left too little of it.

The composite hydrogenation catalyst typically is prepared using a core support material having a surface area of from about 5 to about 400 m$^2$/g, and preferably from about 30 to about 200 m$^2$/g.

Catalysts which can be employed in the hydrogenation process of the present invention include catalysts comprising known catalytic materials for the selective hydrogenation reaction which catalytic materials are supported on an alkoxide-modified support. Examples of said catalyic materials include materials comprising palladium, nickel, platinum, osmium, rhodium, and mixtures thereof, with palladium being preferred. A promoter is optionally employed. Example of typical promoters include Mo, Fe, Cr and metals of Group IB.

The catalytic material is employed in a catalytic amount. Preferably, from about 0.01 to about 1 weight percent catalytic metal is employed in the composite catalyst for selective hydrogenation, more preferably from about 0.02 to about 0.5 weight percent catalytic metal is employed.

The composite catalyst is prepared according to known methods of applying a catalytic material to a support. This may be effected by a dry procedure, such as sputtering, but is preferably effected by a wet process, in which a solution of a palladium compound, for example the chloride or nitrate is applied to the support by, for example, dipping or spraying. Spraying is preferred in order to obtain more reliably the desired uptake of palladium. Penetration of palladium can be controlled by suitable adjustment of the acidity of the solution, the acidity level being dependent on the alkali content of the alumina. If desired, the deposition of the palladium can be aided by a precipitant such as a slow-acting alkali (for example urea) or a reducing agent.

A preferred hydrogenation catalyst has the catalytic metal located below the surface of the alkoxide-modified composite support, and is prepared using an acidic solution of an acid such as, for example, HF, which is preferred, or citric acid or other acids. For example, the typical concentration of HF in the catalytic metal-containing solution is from about 1 to about 8 weight percent. The average penetration of palladium into the support preferably is from about 0.01 mm to about 1 mm below the surface of the composite catalyst. The method of preparing such a penetrated layer catalyst is well-known. See, e.g., *Journal of Catalysis*, V. 51, pp. 185–192 (1978).

After application of the palladium content to the support, it is drained. They may be dried at a temperature in the range of 25° C. to 150° C., conveniently at about 100° C., and may, without or with a distinct drying step, be heated to decompose the palladium compound, suitably at a temperature up to 500° C., especially in the range of 150° C. to 450° C. The pieces may be treated with hydrogen to complete reduction to palladium metal for example during the heating step just mentioned and/or during an additional heating step (in which the temperature should be in the range of 25° C. to 450° C.) after the first heating step but before use. If there is no preliminary reduction step, reduction takes place under the reducing conditions in the selective hydrogenation process. If the catalyst is reduced before use, it may be stored under an inert atmosphere but should preferably not be kept for prolonged periods in hydrogen. If desired, the composite catalyst can be reduced in a known manner using a known reducing agent such as hydrazine or sodium borohydride, $NaBH_4$. The use of $NaBH_4$ as a reducing agent is well-known. See, e.g., *Catal. Rev. - Sci. Eng.*, 14(2), 211–246 (1976).

For the purposes of the hydrogenation process of the present invention, the terms conversion and selectivity are as defined in *Applied Catalysis*, V. 2, pp. 1–17 (1982). Surprisingly, the hydrogenation catalyst of the present invention produces relatively little green oil, i.e., alkyne oligomers.

The following examples and comparative experiments are given to illustrate the invention and should not be construed as limiting its scope. All parts and percentages are by weight unless otherwise indicated.

Specific Embodiments

Preparation of Alkoxide-Modified Supports

Preparation 1

A solution 4.5 g of $Al(OCH(CH_2CH_3)(CH_3))_3$, obtained from Alfa Products, a Division of Morton Thiokol, Inc., in 20 ml of hexanes is added to a suspension of 10 g of $\gamma$-$Al_2O_3$ core support material, obtained from Strem Chemicals, Inc., and having a BET surface area of 100 m$^2$/g in 125 ml of hexanes to form a mixture. The mixture is stirred for 2 hours at room temperature under an inert atmosphere. Then the hexanes are removed under vacuum to yield a white powder. The powder is calcined in air at 450° C. for 15 hours to form an $AlO_x$/$\gamma$-$Al_2O_3$ alkoxide-modified support having a BET surface area of 120 m$^2$/g. The weight ratio of $AlO_x$ to $\gamma$-aluminum is approximately 0.05. The BET surface area of the modified support is 120 m$^2$/g, versus 100 m$^2$/g for the unmodified alumina. Thus, the alkoxide modification does not significantly alter the overall surface area of the support. Other physical data for the treated and untreated aluminas of Preparation 1 are as follows:

| | $\gamma$-alumina | $AlO_x$/$\gamma$-alumina |
|---|---|---|
| pore volume (cc/g) | 0.27 | 0.23 |
| average pore size (A) | 60 | 45 |

For the purposes of the present invention, the subscript "x" in the term $AlO_x$ represents the relative number of oxygen atoms in an alkoxide-modified support which are associated with the metal of the metal alkoxide. While not wishing to be bound by this statement, it is believed that the metal(s) of the metal oxide layer of the modified support are in the highest oxidation state, based on calcination conditions. While this example employs $AlO_x$, additional examples of preferred metals of the metal alkoxide are listed hereinabove.

Preparation 2

The procedure of Preparation 1 is followed except that the precursor metal alkoxide is $Ti(OCH(CH_3)_2)_4$, and the final product alkoxide-modified support is $TiO_x$/$\gamma$-$Al_2O_3$.

Preparation 3

The procedure of Preparation 1 is repeated except that the precursor metal alkoxide is $Ta(OCH(CH_3)_2)_4$, and the alkoxide-modified support is $TaO_x$ on $\gamma$-$Al_2O_3$.

Preparation 4

The procedure of Preparation 1 is repeated with the following exceptions:

(a) 9 g of the aluminum alkoxide is employed;

(b) the core support material is 20 g of 30–80 mesh $\gamma$-$Al_2O_3$ (obtained from United Catalyst, Inc. under the designation T-374 and having a surface area of approximately 100 m$^2$/g) and is suspended in 50 ml of hexane; and (c) the powder is calcined at 550° C. for 5 hours.

The resulting alkoxide-modified support contains 5 weight percent (based on aluminum) of aluminum oxide ($AlO_x$) coating.

Preparation 5

The procedure of Preparation 4 is repeated expect that 50 g of the core support material are treated with 4.5 g of the aluminum alkoxide, and the powder is calcined at 450° C. in air overnight.

EXAMPLE 1 - METHANATION CATALYST PREPARATION

Five grams of the support of Preparation 1 are added to a 100-ml solution of 0.64 g of $RuCl_3$ (1–3 $H_2O$) in $H_2O$. The mixture is stirred for an hour and the water is removed under vacuum with steam heat. The solids are dried overnight at 110° C. in air. Analysis indicates that the solids contain 5 weight percent Ru.

General Methanation Reaction Procedure

A 16-inch long piece of 9/16 inch tubing of type 316 stainless steel is employed vertically as a reactor. The reactor is equipped with a means for temperature control, and has 1 g of catalyst held in place by quartz wool in the center of the reactor. The catalyst is reduced in situ at 400° C. for 15 hours with hydrogen at 50 cc/min. Then the reactor is cooled to 300° C. in flowing hydrogen gas. Then a feed stream consisting of 2 moles of hydrogen per mole of carbon monoxide is fed to the reactor under a pressure of 1 atmosphere (14.7 psig) at 100 cc/min (gas hourly space velocity=6000/hr). The product stream is analyzed using gas chromatographic methods capable of detecting $C_1$–$C_5$ hydrocarbons, $C_1$–$C_5$ alcohols, $H_2$, CO, and $CO_2$.

EXAMPLES 2-5 AND COMPARATIVE EXPERIMENTS 1-4

The General Methanation Reaction Procedure is followed for Examples 2-5 and Comparative Experiments 1-4, and each run is conducted for a 24-hour period. The results of each run are summarized in Table I.

EXAMPLE 2

The catalyst of Example 1 is employed.

COMPARATIVE EXPERIMENT 1

The catalyst is 5 weight percent Ru on the $\gamma$-$Al_2O_3$ core support material of Preparation 1 with no alkoxide modification.

EXAMPLE 3

The catalyst is 5 weight percent Ru on the support of Preparation 2.

COMPARATIVE EXPERIMENT 2

The catalyst is 5 weight percent Ru on $TiO_2$, the untreated $TiO_2$ having a BET surface area of 100 m²/g.

EXAMPLE 4

The catalyst is 5 weight percent Ru on the support of Preparation 3.

COMPARATIVE EXPERIMENT 3

The catalyst is 5 weight percent Ru on $Ta_2O_5$, the untreated $Ta_2O_5$ having a BET surface area of 5 m²/g.

TABLE I

| | Methanation Results with 5 Weight Percent Ruthenium Catalysts | | |
|---|---|---|---|
| Run | Catalyst | Conversion of CO (mole %) | Selectivity to Methane (mole %) |
| Ex. 2 | Ru/$AlO_x$/$\gamma$-$Al_2O_3$ | 99 | 100 |
| C.E. 1 | Ru/$\gamma$-$Al_2O_3$ | 62 | 99 |
| Ex. 3 | Ru/$TiO_x$/$\gamma$-$Al_2O_3$ | 98 | 100 |
| C.E. 2 | Ru/$TiO_2$ | 58 | 100 |
| Ex. 4 | Ru/$TaO_x$/$\gamma$-$Al_2O_3$ | 97 | 100 |
| C.E. 3 | Ru/$Ta_2O_5$ | 17 | 37 |

The results summarized in Table I indicate that the catalyst of the present invention unexpectedly and significantly outperforms, under identical conditions, conventional catalysts supported on materials used as the core support material of the catalyst of the present invention.

EXAMPLE 5 AND COMPARATIVE EXPERIMENT 4

Example 2 and Comparative Experiment 1 are repeated except that the catalyst has 1 weight percent ruthenium. The results are summarized in Table II.

TABLE II

| | Methanation with 1 Weight Percent Ruthenium Catalyst | | |
|---|---|---|---|
| Run | Catalyst | Conversion of CO (mole %) | Selectivity to $CH_4$ (mole %) |
| Ex. 5 | Ru/$AlO_x$/$\gamma Al_2O_3$ | 90 | 99 |
| C.E. 4 | Ru/$\gamma$-$Al_2O_3$ | 3 | 81 |

Surprisingly, at the lower catalyst loading, 1 weight percent ruthenium, the catalyst of the present invention significantly outperforms the equivalent catalytic metal on the conventional support. More surprisingly, a loading of 1 weight percent ruthenium on an alkoxide-modified support outperforms a conventional catalyst having a loading of 5 weight percent ruthenium (see Comparative Experiment 1).

COMPARATIVE EXPERIMENT 5

Comparative Olefin Metathesis Catalyst Preparation

Three grams of the T-374 alumina employed in Preparation 4 is added with stirring to a 30-ml aqueous solution of perrhenic acid for 1 hour. The acid perrhenic solution contains 0.096 g of rhenium metal. The mixture is evaporated to dryness on a steam bath. The dry powder is calcined in a 50-ml per minute stream of air at 575° C. for 9 hours, and for 3 hours in a 50-ml per minute stream of nitrogen. The calcined powder is then cooled to room temperature under a nitrogen atmosphere. Analysis by plasma emission spectroscopy indicates a 2.96 weight percent rhenium loading.

EXAMPLE 6 - OLEFIN METATHESIS CATALYST PREPARATION

The catalyst is prepared using the procedure of Comparative Experiment 5 except that the support is 2.1 g of the modified gamma alumina of Preparation 4, and the perrhenic acid solution contains 0.13 g of rhenium and 50 ml of water. Analysis by plasma emission spectroscopy indicates a 3.01 weight percent rhenium loading.

General Olefin Metathesis Reaction Procedure

A reactor is employed which is similar to the reactor of the general methanation reaction procedure except that the diameter is ⅜ inch. The catalyst is activated in situ at 550° C. for 2 hours with nitrogen at 50 ml per minute. The reactor is then cooled to 87° C. in flowing nitrogen. A feed stream is then fed to the reactor under a pressure of 1 atmosphere gauge and a gas hourly space velocity of from 100 to 1000 hours$^{-1}$. The product stream is analyzed using a capillary gas chromatograph.

COMPARATIVE EXPERIMENT 6 AND EXAMPLE 7

The general olefin metathesis reaction procedure is followed. The feed stream is a mixture of 25 mole percent propylene in helium. Data obtained using the comparative catalyst of Comparative Experiment 5 is summarized in Table III. Data obtained using the catalyst of Example 6 is summarized in Table IV. In each case, the conversion is monitored by the disappearance of propylene from the reactor effluent. Ethylene and 2-butenes are the only products observed. The conversion is thermodynamically limited to 37 percent under the given reacton conditions. The conversion is calculated according to the formula:

$$\% \text{ conversion} = \frac{\text{moles of propylene converted}}{\text{moles of propylene fed}} \times 100$$

TABLE III

Propylene Metathesis Over $Re_2O_7/Al_2O_3$*

| Time (H) | GHSV ($H^{-1}$) | Conversion (%) |
|---|---|---|
| 1 | 100 | 17.7 |
| 16 | 100 | 13.8 |
| 23.5 | 100 | 12.0 |
| 23.6 | 500 | 3.6 |
| 23.8 | 800 | 1.6 |
| 42.7 | 100 | 8.8 |
| 46.8 | 100 | 9.6 |

*1.0 gram catalyst, 2.96 weight percent Re, 30–80 mesh, 360K, 0.1 MPa.

TABLE IV

Propylene Metathesis Over $Re_2O_7$/Modified $Al_2O_3$*

| Time (H) | GHSV ($H^{-1}$) | Conversion (%) |
|---|---|---|
| 50.5 | 110 | 27.2 |
| 68 | 300 | 14.6 |
| 70 | 500 | 6.5 |
| 70.8 | 1000 | 3.4 |
| 71.5 | 100 | 16.1 |
| 73.8 | 100 | 17.6 |

*1.0 gram catalyst, 3.01 weight percent Re, 5.0 weight percent Al coating, 30–80 mesh, 360K, 0.1 MPa.

From Tables III and IV it is observed that the catalyst of the present invention unexpectedly gives higher conversion over a longer period of time as compared to a comparative catalyst prepared using a conventional support material.

COMPARATIVE EXPERIMENT 7 AND EXPERIMENT 8

Following the General Olefin Metathesis Reaction Procedure, the reactor is fed pure isobutylene at 10 milliliters per minute. Only oligomerization of isobutylene is observed. After a period of time, as mentioned hereinbelow, the propylene/helium feed of Example 7 is resumed and the isobutylene feed is discontinued. Significant deactivation of the catalyst of Comparative Experiment 6 is observed after isobutylene has been fed to the reactor for 5 hours. Specifically, the activity for the metathesis reaction decreases 80 mole percent, based on propylene converted. After 15 hours of prior isobutylene feed, the catalyst is totally deactivated. In contrast, the catalyst of Example 7 exhibits much less deactivation with isobutylene and after 23 hours of prior isobutylene feed the activity decreases by only 25 percent. Thus, the catalyst of the present invention is shown to be less prone to deactivation.

General Carbonylation Reaction Procedure

The reactor is a Hastelloy B ½-inch diameter fixed bed tubular reactor. The fixed bed of the reactor is created by first loading 5.0 ml of α-alumina pellets, then 10.0 ml of 10–20 mesh catalyst, and finally 3 ml of quartz chips. The catalyst is first reduced under flowing hydrogen at 400 cc per minute at 250° C. for 2 hours. The reaction is carried out at a temperature of 210° C., a total pressure of 600 psig, a carbon monoxide flow rate of 25 cc per minute (GHSV=150), and at a liquid feed rate of 7.2 cc per hour. The molar ratio of the liquid feed is 2.0 methanol:0.2 cyclohexane (internal standard):1.0 2-chloropropene.

EXAMPLE 9

Preparation of Carbonylation Catalyst

An 11.16-g sample of an alkoxide modified support prepared according to the procedure of Preparation 4 is heated to 120° C. and is held at that temperature for several hours. A solution having a pH of 3 is prepared by adding 0.57 g of $PdCl_2$ to 15 ml of deionized water and 1.2 ml of concentrated hydrochloric acid, and heating the resulting mixture to 70° C. The heated support is contacted with the hot palladium chloride solution using the incipient wetness technique. The impregnated palladium catalyst is allowed to cool to room temperature and then is heated to 120° C. for 2 hours in a stream of air. The catalyst is loaded into the reactor and is reduced as described in the general carbonylation reaction procedure. Measurements of crystallites sized by hydrogen chemisorption show that the catalyst has a palladium dispersion of 56 percent and a loading of 3.0 weight percent palladium based on total catalyst weight. The results which are obtained using this catalyst in the General Carbonylation Reaction Procedure are summarized in Table V.

COMPARATIVE EXPERIMENT 8

Comparative Carbonylation Catalyst Preparation

The comparative carbonylation catalyst is prepared using a 3.2 weight percent palladium on γ-alumina catalyst available from the Calsicat Division of Mallinckrodt, Inc. under the designation: sample #21C-095B.

The catalyst is reduced according to the procedure of Example 9. The palladium dispersion is 38 percent. The results obtained using this catalyst in the General Carbonylation Reaction Procedure are summarized in Table V.

TABLE V

| Carbonylation | | | |
|---|---|---|---|
| Ex. 9 | | C.E. 8 | |
| Time (h) | % Conversion | Time (h) | % Conversion |
| 22 | 52 | 3 | 50 |
| 25 | 49 | 4 | 49 |
| 42 | 45 | 7 | 47 |
| 45 | 43 | 25 | 36 |
| 65 | 38 | 27 | 38 |
| 71 | 34 | 31 | 36 |
| 90 | 28 | 48 | 28 |
| 100 | 28 | 60 | 25 |
| | | 70 | 24 |

Inorganic [$Cl^-$] in product stream:
Ex. 9 - ≦ 120 mg/l
C.E. 8 - ≧ 360 mg/l

It is apparent from Table V that the carbonylation catalyst of the present invention exhibits greater activity and has a longer lifetime than the comparative catalyst. It is noted that use of the catalyst of Ex. 9 results in a lower chloride ion concentration in the product stream, i.e., the product stream advantageously is less corrosive when employing the catalyst of Ex. 9.

COMPARATIVE EXPERIMENT 9

Comparative Hydrogenation Catalyst

A 10-cc sample of the untreated T-374 alumina of Preparation 4 is impregnated for 15 minutes with an excess of an aqueous solution of palladium nitrate which contains 0.08 weight percent palladium. Then, the impregnated support is separated from the excess solution and is rinsed with distilled water. The resulting wet catalyst is then placed in a solution of NaBH$_4$ (at least 10 molar equivalents based on palladium) to reduce the palladium ions to palladium metal. The wet catalyst remains in solution for a period of 30 minutes. The excess solution is then separated from the catalyst pellets and the pellets are rinsed with acetone, to deactivate any residual NaBH$_4$, and are allowed to dry in air. The resulting catalyst has about 0.05 weight percent palladium by analysis.

EXAMPLE 10

Hydrogenation Catalyst Preparation

The procedure of Comparative Experiment 9 is repeated except that the catalyst support is the alkoxide-modified support of Preparation 5.

EXAMPLE 11

Hydrogenation Catalyst Having Sub-surface Palladium

The procedure of Comparative Experiment 9 is repeated except that the catalyst support is the alkoxide-modified support of Preparation 5. An additional exception is that the palladium solution contains four weight percent hydrofluoric acid.

The catalyst of Ex. 11 is in the form of cylindrical pellets ⅛" by ⅛". The color is gray to gray/white. Cutting a pellet in half exposes a dark gray to black band of reduced palladium which is approximately 0.1 to 0.5 mm below the surface. The band is very narrow, having a width of approximately 0.05 to 0.1 mm. The light gray coloration may penetrate to about 1 mm below the surface and the inside of the pellet is white. The alkoxide treatment deposits one weight percent, based on aluminum, of Al$_2$O$_3$ on the surface of the gamma alumina core support. The impregnation using 0.08 weight percent palladium and a four weight percent HF solution produces a palladium loading of about 0.05 weight percent.

General Hydrogenation Reaction Procedure

Ten cc of catalyst is placed into a 300-cc Berty reactor. A feed stream containing 0.5 mole percent H$_2$, 0.5 mole percent C$_2$H$_2$, 5 ppm CO, and approximately 99.5 mole percent ethylene (containing small amounts of ethane and methane) is introduced to the reactor at a rate of 0.5 liters per minute (gas hourly space velocity equal 3,000 hours$^{-1}$) and a pressure of 250 psig. The reactor effluent is analyzed by gas chromatograph. The conversions of acetylene and hydrogen are measured directly, as is the selectivity to ethane and C$_4$ compounds. The change in ethylene concentration and green oil production values is calculated, assuming no hydrogen is consumed in the green oil, using the method of Battiston et al. in *Applied catalysis*, Vol. 2, pages 1–17 (1982). The results in mole percent are summarized in Table VI.

TABLE VI

| Catalyst of: | Temp (°C.) | Hydrogenation with Pd on γ-Alumina Catalyst | | | | | |
|---|---|---|---|---|---|---|---|
| | | Conversion | | Selectivity | | | |
| | | C$_2$H$_2$ | H$_2$ | C$_2$H$_4$ | C$_2$H$_6$ | C$_4$'s* | GO* |
| C.E. 9 | 40 | 33.1 | 19.6 | 41.5 | 8.8 | 8.5 | 41.5 |
| | 50 | 54.4 | 32.4 | 42.5 | 6.7 | 11.6 | 39.5 |
| | 60 | 80.1 | 49.5 | 45.6 | 6.1 | 12.1 | 36.4 |
| Ex. 10 | 40 | 89.7 | 50.1 | 38.8 | 8.4 | 12.1 | 40.9 |
| | 50 | 95.6 | 75.1 | 31.5 | 12.6 | 16.7 | 28.4 |
| | 60 | 97.4 | 84.0 | 36.1 | 26.7 | 15.2 | 22.4 |

TABLE VI-continued

| Catalyst of: | Temp (°C.) | Hydrogenation with Pd on γ-Alumina Catalyst | | | | | |
|---|---|---|---|---|---|---|---|
| | | Conversion | | Selectivity | | | |
| | | C$_2$H$_2$ | H$_2$ | C$_2$H$_4$ | C$_2$H$_6$ | C$_4$'s* | GO* |
| Ex. 11 | 40 | 87.2 | 53.0 | 41.5 | 8.3 | 16.2 | 34.2 |
| | 50 | 93.8 | 69.4 | 36.1 | 21.4 | 12.4 | 30.4 |
| | 60 | 95.8 | 83.9 | 26.4 | 33.6 | 14.6 | 26.3 |

*Expressed as moles of C$_2$H$_2$
GO = green oil

From Table VI it can be seen that the catalysts of the present invention (Examples 10 and 11) are more active and produce relatively less green oil, or oligomers, as compared to the catalyst of C.E.9, which has a conventional support.

COMPARATIVE EXPERIMENTS 10–11

Comparative catalysts are prepared using the methods of Examples 10 and 11, except that the alumina core support is α-alumina having a surface area of about 4 m$^2$/g. The α-alumina is obtained from Harshaw Chemical Company under the designation Al-3980. Specifically, the catalyst of Comparative Experiment 10 is prepared in a manner similiar to the manner in which the catalyst of Ex. 10 is prepared. The catalyst of Comparative Experiment 11 is prepared in a manner similiar to the manner in which the catalyst of Ex. 11 is prepared.

The catalysts of Comparative Experiments 10–11 are employed in the General Hydrogenation Reaction Procedure, and the results are summarized in Table VII.

TABLE VII

| Example | Temp (°C.) | Hydrogenation with Pd on α-Alumina Catalyst | | | | | |
|---|---|---|---|---|---|---|---|
| | | Conversion | | Selectivity | | | |
| | | C$_2$H$_2$ | H$_2$ | C$_2$H$_4$ | C$_2$H$_6$ | C$_4$'s* | GO |
| C.E. 10 | 40 | 20.6 | 19.1 | 28.8 | 37.5 | 5.0 | 30.4 |
| | 50 | 32.6 | 29.4 | 24.7 | 35.7 | 9.0 | 32.2 |
| | 60 | 45.9 | 41.7 | 21.7 | 35.6 | 11.1 | 32.9 |
| C.E. 11 | 40 | 24.3 | 15.3 | 50.5 | 12.8 | 6.9 | 35.8 |
| | 50 | 43.8 | 25.8 | 42.4 | 10.8 | 10.9 | 40.9 |
| | 60 | 67.1 | 42.6 | 44.9 | 13.0 | 11.0 | 37.0 |

*Expressed as moles of C$_2$H$_2$
GO = green oil

A comparison of the results of Tables IV and VII surprisingly indicates that alkoxide-modified catalysts with the α-alumina core support having a surface area of 4 m$^2$/g are not drastically improved as in the case when using γ-alumina having a surface area of 100 m$^2$/g as the core support material.

EXAMPLE 12 AND COMPARATIVE EXPERIMENT 12

Extended Hydrogenation Run

Figure 2:
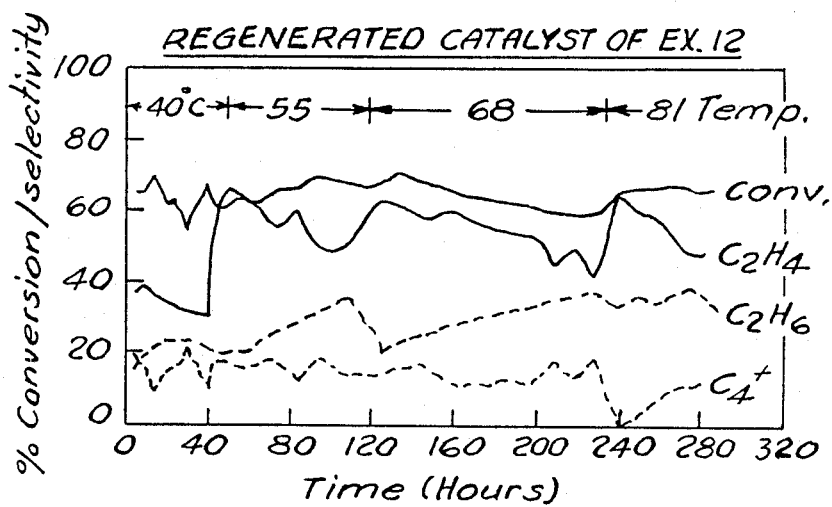
Figure 3:
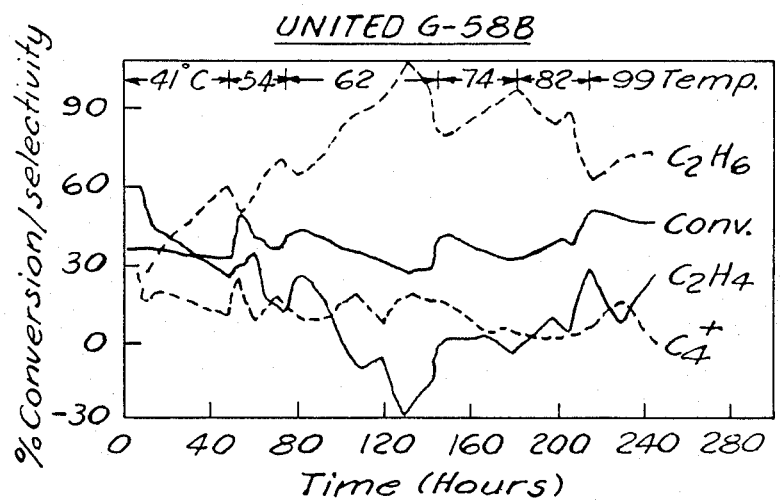
Figure 4:
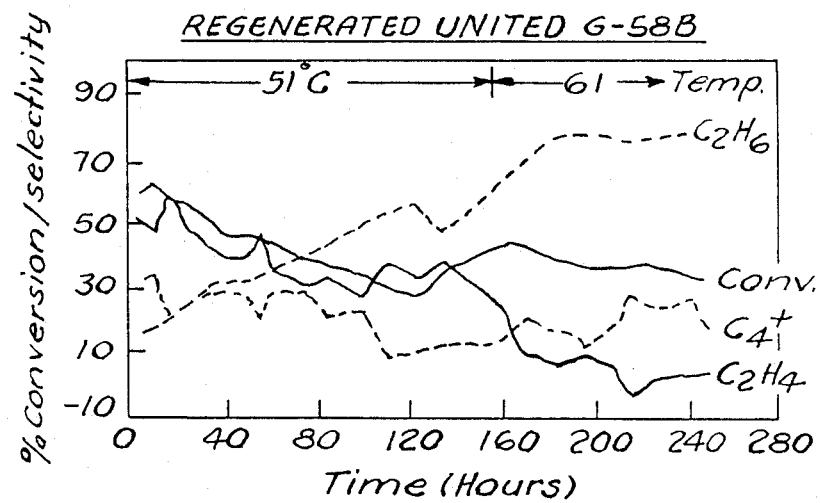

The catalyst of Example 11 and a comparative catalyst are employed in the General Hydrogenation Reaction Procedure. The comparative catalyst is a commerical catalyst available under the designation G-58B, and is available from United Catalysts, Inc. Two runs are done for each catalyst. Fresh catalysts are used in the first runs. The catalysts are regenerated prior to the second runs. The results are summarized in FIGS. 1–4, as indicated:

| Run | Catalyst | FIG. |
| --- | --- | --- |
| Ex. 12A | Ex. 11 | 1 |
| Ex. 12B | Regenerated Ex. 11 | 2 |
| C.E. 12A | G-58B | 3 |
| C.E. 12B | Regenerated G-58B | 4 |

A review of FIGS. 1-4 indicates that the catalyst of the present invention is generally superior to the commercial catalyst regarding conversion of acetylene and selectivity to ethylene.

A review of the Examples indicates that catalysts employing an alkoxide-modified support comprising alumina on alumina having a surface area greater than about 5 $m^2/g$ surprisingly outperform similar catalysts having conventional supports. This is unexpected in that one could possibly expect that a metal oxide/metal oxide support having the same metal, e.g., alumina on alumina, would behave in a manner similar to an untreated support. Thus, one preferred embodiment of the present invention is a catalyst composition wherein the alkoxide-modified support employs the same metal in the metal alkoxide and the core support.

The preceding examples serve only to illustrate the invention and its advantages, and they should not be interpreted as limiting since further modifications of the disclosed invention will be apparent to those skilled in the art. All such modifications are deemed to be within the scope of the invention as defined by the following claims.

What is claimed is:

1. A catalyst composition comprising a catalytic metal and an alkoxide-modified support, which support comprises a core support material having (a) a surface area which is greater than about 5 $m^2/g$; and having (b) on the outer surface thereof a metal oxide produced from a precursor metal alkoxide.

2. The composition of claim 1 wherein the catalytic metal is a Group VIII metal.

3. The composition of claim 1 wherein the core support is a metal oxide.

4. The composition of claim 1 wherein the alkoxide anion of the metal alkoxide has from 1 to about 10 carbon atoms.

5. A catalyst composition consisting essentially of the composition of claim 1.

6. The composition of claim 1 wherein the catalytic metal is from about 0.01 to about 20 weight percent of the total composition.

7. The composition of claim 6 wherein the metal oxide layer prepared from the metal alkoxide is from about 0.1 to about 50 weight percent of the total composition.

8. The composition of claim 7 wherein the core support material is silica or alumina, the catalytic metal is from about 0.02 to about 10 weight percent of the composition, and the metal oxide from metal alkoxide is from about 1 to about 5 weight percent of the composition.

9. The composition of claim 1 wherein the metal of the metal alkoxide is a metal of Group IIIA, IVA, IVB or VB.

10. The composition of claim 1 wherein the alkoxide anion of the metal alkoxide has from about 2 to about 4 carbon atoms.

11. The composition of claim 1 wherein the metal of the metal alkoxide is aluminum, tantalum, or titanium and the catalytic metal is ruthenium.

12. A method of increasing the catalytic activity of a catalytic metal, the method comprising supporting the catalytic metal on a support prepared by contacting a metal alkoxide with a core support material, which support has a surface area which is greater than about 5 $m^2/g$; then treating the mixture of the metal alkoxide and the core support material to remove the carbon atoms therefrom, thereby leaving a coating on the core support, the coating comprising the metal oxide from the metal alkoxide.

13. The method of claim 12 wherein the treating step to remove the carbon atoms is a step comprising calcination.

14. The method of claim 12 wherein the core support is an oxide of a metal of Group IIIA, IVA, IVB or VB.

15. The method of claim 12 wherein the metal of the metal alkoxide salt is a metal of Group IIIA, IVA, IVB or VB.

16. The method of claim 12 wherein the catalytic metal is a metal of Group VIII.

* * * * *